United States Patent [19]

Gosser

[11] 3,966,595

[45] June 29, 1976

[54] METHOD OF MAKING GROUP VIII METAL COMPLEX COMPOUNDS

[75] Inventor: Lawrence W. Gosser, Wilmington, Del.

[73] Assignee: E. I. Du Pont de Nemours and Company, Wilmington, Del.

[22] Filed: May 10, 1974

[21] Appl. No.: 468,691

Related U.S. Application Data

[63] Continuation of Ser. No. 273,804, July 20, 1972, abandoned.

[52] U.S. Cl. .......................... 260/429 R; 252/426; 210/23 H
[51] Int. Cl.² ................................ B01D 13/00
[58] Field of Search ............ 210/23; 252/431, 426; 260/448, 475, 990

[56] References Cited
UNITED STATES PATENTS

| | | |
|---|---|---|
| 3,567,632 | 3/1971 | Richter et al. .................. 210/23 |
| 3,617,553 | 11/1971 | Westaway et al. ............... 210/23 |
| 3,798,256 | 3/1974 | King et al. .................. 260/465.8 R |
| 3,853,754 | 12/1974 | Gosser ......................... 210/23 |

FOREIGN PATENTS OR APPLICATIONS

| | | |
|---|---|---|
| 729,810 | 3/1969 | Belgium ........................ 210/23 |
| 741,956 | 10/1969 | Belgium ........................ 210/23 |
| 1,243,507 | 8/1971 | United Kingdom ............... 210/23 |
| 1,243,508 | 8/1971 | United Kingdom ............... 210/23 |
| 1,266,180 | 3/1972 | United Kingdom ............... 210/23 |

Primary Examiner—Theodore A. Granger

[57] ABSTRACT

Reverse osmosis is employed to remove neutral ligands (usually phosphines, phosphites, stibines or arsines) from solutions of dissociable Group VIII metal complexes whereby a ligand-deficient reactive complex (which may be further reacted) is obtained. The products are useful as catalysts and as absorbants for carbon monoxide or acetylene.

11 Claims, No Drawings

METHOD OF MAKING GROUP VIII METAL COMPLEX COMPOUNDS

CROSS-REFERENCE TO RELATED APPLICATION

This is a continuation of my earlier copending Ser. No. 273,804, filed July 20, 1972, now abandoned.

BACKGROUND OF THE INVENTION

This invention relates to a method of making certain relatively reactive organometallic complex compounds using reverse osmosis.

Organometallic complex compounds have frequently found utility in catalyst systems. In many instances the catalysts operate by the formation of weak complexes with one or more reactants. It is frequently found that the catalytic species is a ligand-deficient species, or a species containing one or more ligands which are readily displaced by a reactant molecule. Such species are often highly reactive and cannot be isolated by direct chemical methods.

The present invention is therefore directed to a process of producing reactive organometallic complexes by reverse osmosis techniques.

Reverse osmosis is a well known technique which has been employed in a wide variety of applications. Thus U.S. Pat. No. 3,567,632 to J. W. Richter and H. H. Hoehn teaches the preparation of permselective membranes and their use in the desalination of water. Reverse osmosis has been used to separate complexes from a homogeneous fluid mixture using polyolefin membranes (Netherlands Pat. No. 70/08849 to British Petroleum). Similar disclosures teaching the use of cellulosic and of silicone membranes are found in British Pat. Nos. 1,243,507 and 1,243,508 respectively.

The variables in these processes are so chosen as to decrease the concentration of the transition metal complex in the permeate. The examples show separation of the rhodium complex $Rh(Bu_3P)CO$ (acetylacetonate), from toluene or heptaldehyde solvents, the latter having been formed by the rhodium complex-catalyzed hydroformylation of hexene. The catalyst solution, now at increased concentration, is recycled.

British Pat. No. 1,212,758 teaches that poly(vinyl pyrrolidone) is separated into fractions of differing molecular weight by contacting a solution of the poly(vinyl pyrrolidone) with the upstream side of a fluid permeable microporous anisotropic membrane under a pressure greater than the pressure on the second, downstream side, thereby forcing a portion of the poly(vinyl pyrrolidone) through the membrane. Among the suitable membrane materials for this process are included polyamides and polyimides.

SUMMARY OF THE INVENTION

The process of the present invention is a method of making Group VIII metal complex compounds which comprises:

contacting a solution containing a complex of a Group VIII metal having at least one reversibly dissociable neutral ligand with a semipermeable membrane permeable to said ligand, and applying pressure greater than the osmotic pressure of the system whereby said ligand is separated from said solution.

DETAILED DESCRIPTION OF THE INVENTION

The Group VIII metal complexes which are employed in this invention can be described by the formula $$L_xMY_z$$

wherein M is a group VIII metal;
L is a neutral dissociable ligand, and the Y's, alike or different are anionic ligands or noncoordinated counter-ions, including hydride (H), halides (F, Cl, Br, I) and 1,3-diphenyltriazinides;
x is 3–6 inclusive;
z is 0 to 3 inclusive.

The Group VIII metal complexes in solution dissociate reversibly:

$$L_xMY_z \rightleftarrows [L_{x-1}MY_z] + L$$

The process of the present invention is essentially directed to the production of ligand deficient species either as the final product or as an intermediate by physical removal of the ligand L from solution.

In particular, this invention is valuable in making species wherein the equilibrium in the above-formulated reversible reaction lies well to the left of the equation: that is in the production of reactive species which are difficult or impossible to obtain by direct chemical methods.

As an example of a ligand deficient species which can be obtained directly by the process of this invention, tetrakis-(tri-o-tolylphosphite)nickel can be converted to tris(tri-o-tolylphosphite)nickel as shown in Example 1 hereinbelow.

As an example of the case wherein the ligand deficient species is an intermediate, there is the production and isolation of triphenylphosphine ruthenium hydride complex with nitrogen according to the equation

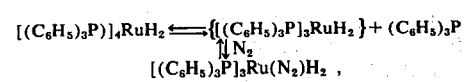

as shown by Examples 2 and 3. This complex was reported to be formed in solution by A. Yamamoto et al., J. Am. Chem. Soc. 90, 1089 (1968) and to be decomposed by the $(C_6H_5)_3P$ ligand. In this instance the reaction is believed to proceed by unimolecular decomposition of the starting material followed by reaction with nitrogen gas as depicted in the above equation. However, the method of the present invention is equally applicable to bimolecular reactions where the ligand is displaced concurrently with the insertion of the new ligand. Dimerization of the new species may also take place.

Ligands used in this invention are hydrocarbyl- and substituted hydrocarbylphosphines, $PR_3$, —arsines, $AsR_3$, —stibines, $SbR_3$, phosphites, $P(OR)_3$, phosphonites, $RP(OR)_2$, phosphinites, $R_2P(OR)$, phosphinamides, $R_2P(NR_2^1)$, and phosphorous triamides, $P(NR_2^1)_3$.

In the case of hydrocarbylphosphinamides, $R_2P(NR_2^1)$, the nitrogen may be substituted with two monovalent hydrocarbyl groups as described below or by a polymethylene chain containing 4 through 6 carbon atoms. Each R group, alike or different, is an organic radical of up to 12 carbon atoms, preferably a hydrocarbyl radical with up to 3 substituents of lower alkoxy, aryloxy, fluorine, chlorine, lower alkoxycarbonyl, lower acyloxy, cyano, lower alkanesulfonyl and lower acyl, "lower" meaning up to 4 carbon atoms.

The term "hydrocarbyl" refers to a radical derived from a hydrocarbon by removal of a hydrogen atom. Preferably hydrocarbyl is alkyl, cycloalkyl or aryl.

The term "aryl" refers to a hydrocarbyl radical formed from a hydrocarbon having an aromatic ring or rings by removal of a hydrogen atom from a carbon atom of such aromatic ring. As thus defined the term includes radicals, such as p-tolyl, having nonaromatic hydrocarbon substituents on the aromatic nucleus.

The substituent $R^1$ on the nitrogen atom of the phosphinamides includes R as defined above and the two $R^1$ groups jointly can be a polymethylene chain of 4 to 6 carbon atoms.

Exemplary ligands include:
Triethylphosphine
Dimethylphenylphosphine
Diethylphenylphosphine
Triphenylphosphine
Tri-o-tolylphosphine
Tri-m-tolylphosphine
Tri-p-tolylphosphine
Diphenyl-N-piperidinophosphine
Diphenyl-N-pyrrolidinophosphine
Diphenylbenzylphosphine
Triisopentylphosphine
Triisopropylphosphine
Triheptylphosphine
Tri-p-chlorophenylphosphine
Butyldiphenylphosphine
Cyclohexyldiphenylphosphine
Isopropyldiphenylphosphine
Tri(methylcyclopropyl)phosphine
Tricyclohexylphosphine
Dimethyl-p-methoxyphenylphosphine
Dimethyl-p-butylphenylphosphine
Dimethyl-3,4-dimethylphenylphosphine
Diethyl-p-ethoxyphenylphosphine
Diethyl-p-chlorophenylphosphine
Diethyl-1-naphthylphosphine
Tri($\alpha$-naphthyl)phosphine
Tri(4-biphenylyl)phosphine
Tri(dimethylaminophenyl)phosphine
Tri(dimethylamino)phosphine *
Tri-o-methoxyphenylphosphine
Tri-p-methoxyphenylphosphine
Diphenyl-p-tolylphosphine
Isopropyl diphenylphosphinite
Hexyl diphenylphosphinite
Ethyl di(p-chlorophenyl)phosphinite
Butyl diphenylphosphinite
Ethyl diphenylphosphinite
Dibutyl phenylphosphonite
Triphenyl phosphite
Triethyl phosphite
Tri-i-propyl phosphite
Triphenylarsine
Triphenylstibine \* or N,N,N'n',N'',N''-hexamethylphosphorous triamide Metal complexes used in this invention include the following types in which R is as defined above and A is P, $PO_3$, Sb or As:

$(R_3A)_4RuH_2$    $(R_3A)_4CoH$
$(R_3A)_4Ni$       $(R_3A)_4RuCl_2$

-continued $(R_3A)_4Pd$       $(R_3A)_3RuCl_2$
$(R_3A)_4Pt$       $(R_3A)_4FeHCl$
$(R_3A)_4RhH$      $(R_3A)_3RuHCl$ Representative species include:
$[(p-CH_3C_6H_4)_3P]_4RuH_2$     $[(C_6H_5)_3P]_4Pt$
$[(o-CH_3C_6H_4O)_3P]_4Ni$       $[(C_6H_5)_3P]_4Pd$
$[(C_6H_5)_3P]_4RuCl_2$          $[(C_6H_5)_3Ru(H)[N_3(C_6H_5)_2]$
$[(p-CH_3C_6H_4)_3P]_3RuCl_2$    $[(C_6H_5)_3As]_4RuH_2$
$[(C_6H_5O)_3P]_4RhH$            $[(C_6H_5)_3P]_4Ni$ The process of this invention may be carried out in any apparatus capable of performing reverse osmosis and the membrane used is an aromatic polymer having recurring

groups in the polymer chain. Included are aromatic polyamides, aromatic polyimides, aromatic hydrazides and aromatic acyl hydrazides. Exemplary membranes are those disclosed in the aforesaid Richter & Hoehn Pat., Alegranti Ser. No. 273,805, filed July 20, 1972, and Gosser Ser. No. 273,803, filed July 20, 1972.

A preferred form of apparatus employs a multiplicity of hollow fibers arranged in an apparatus as described in the aforesaid Richter and Hoehn patent (FIGS. 5–9, inclusive and column 17, line 8 to column 18, line 75).

A permeator suitable for practicing this invention is described in the Richter and Hoehn reference in FIG. 1, column 15, line 75 to column 16, line 26.

Reverse osmosis and apparatus for this purpose is discussed further in S. Sourirajan, "Reverse Osmosis", Academic Press, New York, 1970.

The permselective membranes used in the practice of this invention are in the form of an asymmetric membrane characterized in having a desnse skin layer on at least one surface or the membrane. The membranes may be in the form of tubes, sheets, or hollow fibers. Such membranes are more fully described in the aforesaid Richter and Hoehn patent and in the Alegranti Ser. No. 273,805.

A preferred class of membranes includes those prepared from the aromatic polymers disclosed in Ser. No. 273,803. These aromatic polymers are composed of arylene groups connected by imide,

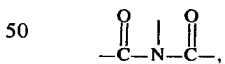

amide,

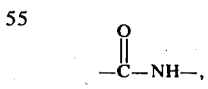

hydrazide,

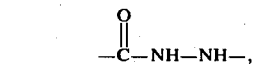

and acyl hydrazide,

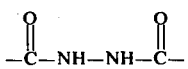

linkages in the polymer chain. Especially preferred aromatic polymers for fabrication of membranes are those prepared from combinations of m- and p-phenylenediamine, 3- and 4-aminobenzhydrazide with iso- and terephthaloyl acid chlorides.

The feed mixture for the reverse osmosis of this invention comprises a Group VIII metal complex and a solvent. Other components that may be present include a ligand dissociated from said Group VIII complex, other dissociation products of a Group VIII metal complex such as anions, cations and other ligands, other solvents and other reactants.

Any common laboratory organic solvent or mixture of solvents may be employed, subject to the limitation that the solvent or solvent mixture not destroy the metal complex or the membrane. In general, solvents are liquid organic compounds containing not more than 12 carbon atoms.

Exposure of the polyimide or polyamide membranes to some liquids causes swelling of the membranes and also sometimes changes in the permeability properties. For example, swelling of a membrane after mounting in a permeation cell may produce wrinkles which can lead to reduced membrane life. Treatment of the membrane with the feed fluid prior to mounting in the cell minimizes subsequent changes. The membrane is mounted in the apparatus with the skin side toward the high pressure or feed side of the apparatus.

The feed mixture is placed in the high pressure side of the reverse osmosis apparatus and pressure is applied by mechanical means or by suitable gas which can be inert or can, if desired, be a reactant itself. The pressure must be in excess of the osmotic pressure. Generally pressures of between 100 and 2500 psi are employed with solutions having an initial concentration of about 1 to 75 wt % of the reactants. Pressure is applied until about 10% to about 90% by volume of solution has permeated the membrane, whereupon the apparatus is depressurized, further solvent added, if desired, to bring the solution to about the original volume and the process is repeated as often as necessary to achieve the desired conversion. One may also operate continuously by pumping solvent into the osmosis cell. Analysis of the effluent is useful in determining the progress of the process.

The temperature at which the process is conducted is not critical. In many cases ambient temperature is employed, but higher or lower temperatures are operable depending on the material selected and the physical properties of the solvent.

SPECIFIC EMBODIMENTS

This invention is further illustrated by the following specific embodiments which are given by way of illustration and should not be construed as fully delineating the scope of this discovery.

The reverse osmosis cell used in all of the following Examples except Example 1 was a commercial Amicon Model 420 cell which has an internal volume of 400 ml and a 76 mm membrane supported by a 2 $\mu$-pore size stainless steel Rigi mesh (sold by Pall Trinity Corp., Cortland, N.Y.). The Amicon Model 420 cell is functionally the same as the cell described in U.S. Pat. No. 3,567,632, FIG. I and col. 15, line 75 to col. 16, line 26.

Membrane Preparation

Membrane I (aromatic polyimide)

1. A dimethylacetamide solution of the polyamide acid ($\eta_{inh}$ c 1.4), prepared from pyromellitic dianhydride and p,p'-diaminodiphenyl ether was diluted to 10 wt. % polymer with dimethylacetamide. One percent by weight of cetyl pyridinium bromide was added and the mixture was tumbled for several hours at room temperature. The solution was filtered with a silver filter (ca 0.5 $\mu$) in a Millipore apparatus under nitrogen pressure. The filtered solution was subjected to reduced pressure briefly to remove trapped gas and stored cold. Before use the solution was warmed to room temperature and gently tumbled to eliminate the concentration gradient produced by the vacuum treatment. This mixing must be done very gently to avoid the production of bubbles. A 0.015 inch layer of this solution was applied to a glass plate at room temperature. After one minute in a gentle stream of air (80°F., 20% humidity) the coated plate was transferred to a room temperature solution of 95 ml acetic anhydride and 140 ml triethylamine in 500 ml of benzene. After 15 minutes at room temperature the bath was warmed to ca 80°C and left for 15 minutes. The plate was then transferred to a room temperature benzene bath and after 15 minutes transferred to a room temperature ethanol bath. The resultant polyimide film was detached from the plate and left for 10 minutes in the ethanol. It was then washed in room temperature water and air-dried.

Membrane II

2. The general procedure described for Membrane I was used. The polymer solution contained 10% polymer and 1% silver pentafluoropropionate. The cyclizing bath was as in Membrane 3 (air temperature, 80°F; humidity, 24%).

Membrane III

3. The general procedure described for Membrane I was used. The casting solution contained 8% polymer, and 0.8% silver trifluoroacetate in dimethylacetamide. The glass plate was dried at 50°C and then cooled to room temperature before use. The cyclizing bath was ca 500 ml of a benzene solution containing 1M triethylamine and 1M acetic anhydride. After washing in ethanol the water wash was omitted and the film was washed in methylene chloride for 15 seconds and then air-dried (air temperature, 80°F; humidity, 12%).

Membrane IV

4. The general procedure described for Membrane I was used. The casting solution contained 10% polymer and 1% silver trifluoroacetate in dimethylacetamide. The cyclizing bath was the same as in Membrane 3 (air temperature 80°F.; humidity 18%). The coated plate was not let stand before transfer to the cyclizing bath.

Membrane V

5. The membrane was prepared as described for Membrane I using a polymer solution containing 10% polymer in dimethylacetamide (air temperature 80°F., humidity 37%).

Membrane VI (aromatic polyamide)

6. An aromatic polyamide membrane was prepared from a dimethylacetamide solution containing 15% of dissolved polymer and 20% each (based on dissolved polymer) of lithium chloride and lithium nitrate. The polymer was prepared from m-phenylenediamine and isophthaloyl chloride. A 25-mil film was cast from this soltuion and heated for 15 minutes by an overhead infrared lamp to a temperature of 40°–45°C. The resulting polymer film was washed well with water for several days and then freeze-dried. The asymmetric membranes are mounted in the permeator with the dense side in contact with the feed.

EXAMPLE 1

The apparatus used in this Example comprised the cell in FIG. I of U.S. Pat. No. 3,567,632 modified with a Rigi mesh screen to support the membrane along with suitable means for applying pressure to the feed mixture. The membrane employed was prepared by method 2 above.

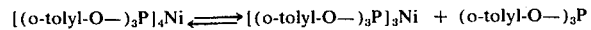

The above tetrakis(tri-o-tolyl phosphite)nickel, a colorless solid partly dissociates in solution as indicated by the equation. A solution of about 1 g of the tetracoordinated nickel complex in 20 ml of benzene was placed in the cell (FIG. II), mounted in a nitrogen-filled dry box. Pressure of 500–700 psi was applied until about 5 ml of permeate had been collected. The pressure was released, an additional 5 ml of benzene added to the cell and the procedure repeated. This procedure was repeated for five cycles. A portion of the remaining feed solution was concentrated to a red grease by evaporating the benzene under reduced pressure. This was converted to a pink powder by treatment with pentane. The selective permeation of the dissociated ligand was clearly indicated by the appearance of the red $[(o\text{-tolyl-O}-)_3P]_3Ni$ in the material recovered from the residual feed solution.

EXAMPLE 2

Cell — Amicon Model 420

Membrane 3

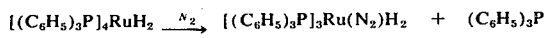

A solution of $[C_6H_5)_3P]_4RuH_2$ (0.5 g) in benzene (60 ml) was charged to a reverse osmosis cell. The cell was pressured to 1200 psi with nitrogen. A light-yellow effluent amounted to 55 ml. The cell was vented and opened in a nitrogen atmosphere. The solution remaining in the cell was diluted with five times its volume of hexane. Crystalline $[(C_6H_5)_3P]_3Ru(N_2)H_2$, identified by infrared analysis, separated.

EXAMPLE 3

Cell — Amicon Model 420

Membrane 4

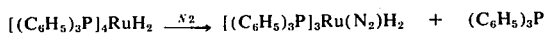

A solution of $[(C_6H_5)_3P]_4RuH_2$ (5 g) in 200 ml of tetrahydrofuran was charged to a reverse osmosis cell fitted with Membrane 4. The cell was pressured to 1400 psi with nitrogen. The cell was vented when 170 ml of effluent had been obtained. The solution (13 ml) was removed from the cell, and 8 ml of this was diluted with an excess of hexane to precipitate crystalline $[(C_6H_5)_3P]_3Ru(N_2)H_2$, identified by infrared analysis. The total yield was 41% of the theoretical.

EXAMPLE 4

Cell — Amicon Model 420

Membrane 5

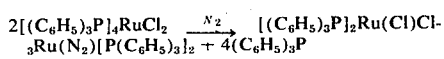

A solution of $[(C_6H_5)_3P]_4RuCl_2$ (4 g) in 200 ml of tetrahydrofuran was charged to a reverse osmosis cell and pressured to 1500 psi with nitrogen. Effluent was removed and additional tetrahydrofuran was added as follows (adding additional tetrahydrofuran required venting and subsequent repressuring of the cell):

| Volume Effluent Removed | Then added ml Tetrahydrofuran |
|---|---|
| 175 | 175 |
| 175 | 100 |
| 100 | 100 |
| 150 | 100 |
| 100 | 100 |
| 100 | — |

The pressure cell was vented and found to contain impure $[(C_6H_5)_3P]_2Ru(Cl)Cl_3Ru(N_2)[P(C_6H_5)_3]_2$, as indicated by comparison of infrared and elemental analytical results with later results from Example 5.

EXAMPLE 5

Cell — Amicon Model 420

Membrane 1

A mixture of 4 g of $[(C_6H_5)_3P]_4RuCl_2$ and 150 ml of tetrahydrofuran was charged to a reverse osmosis cell fitted with Membrane 1. The cell was pressured to 1500 psi with nitrogen. Effluent was removed and additional tetrahydrofuran was added as follows:

| Volume Effluent Removed | Then added ml Tetrahydrofuran |
|---|---|
| 130 | 75 |
| 85* | 125 |
| 60 | 100 |
| 85 | — |

The cell was vented and the contents were rinsed out with tetrahydrofuran and filtered to obtain 1.5 g of $[(C_6H_5)_3P]_2Ru(Cl)Cl_3Ru(N_2)[(C_6H_5)_3]_2$.

Anal. Calcd for $C_{72}H_{60}Cl_4N_2P_4Ru_2$:
C, 60.84; H, 4.25; Cl, 9.97; N, 1.97; P, 8.71
Found: C, 61.11; H, 4.58; Cl, 9.71; N, 1.56; P, 8.56
61.22    4.54    1.62

The infrared spectrum exhibits a strong sharp band at 2165 $cm_+^1$ in dichloromethane solution for the N≡N stretching mode.

EXAMPLE 6

A. Preparation of $[(C_6H_5)_3P]_3Ru(H)[N_3(C_6H_5)_2]$

To a solution of 1.5 g of 1,3-diphenyltriazine in 200 ml of tetrahydrofuran was added 4.5 ml of a 1.6 M solution of n-butyllithium in hexane. An atmosphere of dry nitrogen was maintained throughout the reaction. After the above mixture was stirred for 3 minutes, $[(C_6H_5)_3P]_3RuHCl \cdot C_6H_5CH_3$ (6 g) was added and stirring was continued for 2 hours. The reaction mixture was filtered and the filtrate was evaporated to dryness. The dark residue was digested in boiling hexane, thus converting it to an orange-red solid (5.5 g). Recrystallization of this from benzene/hexane gave 3.2 g of $[(C_6H_5)_3P]_3Ru(H)[N_3(C_6H_5)_2]$; m.p. 197°–200°C.

| C, | 73.04; | H, | 5.20; | N, | 3.87; | P, | 8.56; | Ru, | 9.31; | M.W., 1085 |
|---|---|---|---|---|---|---|---|---|---|---|
| Found: C, | 73.66;<br>73.62 | H, | 5.33;<br>5.47 | N, | 3.85;<br>3.81 | P, | 8.26; | Ru, | 9.70;<br>743, | M.W., 837 |

B. Preparation of $[(C_6H_5)_3P]_2Ru(H)(N_2)[N_3(C_6H_5)_2]$

Cell — Amicon Model 420

Membrane 1

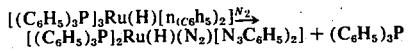

A solution of 2.1 g of $[(C_6H_5)_3P]_3Ru(H)[N_3(C_6H_5)_2]$ in 150 ml of tetrahydrofuran was added to a reverse osmosis cell and pressured to 1300 psi with nitrogen. Effluent was removed and the cell recharged with tetrahydrofuran as follows:

| Volume Effluent Collected | Then added ml Tetrahydrofuran |
|---|---|
| ca 150* | 100 |
| 80 | 50 |
| 50** | 200 |
| ca 200 | — |

* Evaporation of effluent left 0.11 g of triphenylphosphine.
** Evaporation of effluent left a total of 0.32 g of triphenylphosphine.

The solid cake left in the permeator was extracted with a small amount of tetrahydrofuran. The extract was filtered and the filtrate was diluted with hexamethyldisiloxane until it was faintly cloudy. It was allowed to stand for 45 minutes during which time yellow crystals (0.5 g) of $[(C_6H_5)_3P]_2Ru(H)(N_2)[N_3(C_6H_5)_2]$ separated. The crystals were collected on a filter and the filtrate treated with additional hexamethyldisiloxane to cause separation of additional 0.25 g of the same product.

Anal. Calcd for $C_{48}H_{41}N_5P_2Ru$: C, 67.74; H, 4.85; N, 8.23; P, 7.28. Found: C, 68.82; H, 4.96; N, 7.89; P, 6.94.

The presence of complexed dinitrogen was confirmed by a strong sharp infrared absorption band at about 2160 $cm_+^1$.

EXAMPLE 7

Cell — Amicon Model 420

Membrane 6

A solution of 3.0 g of $[(C_6H_5)_3P]_4RuH_2$ in 200 ml of tetrahydrofuran was filtered and the filtrate charged to the reverse osmosis cell, which was then pressured to 1000 psi with nitrogen. Permeation was rapid and was continued until no further effluent was obtained. The cell was opened and the thick viscous mass inside was leached out with ca. 10 ml of tetrahydrofuran. This was diluted with about 100 ml of hexane and allowed to stand for 3 days. Crystalline $[(C_6H_5)_3P]_3Ru(N_2)H_2$ (0.13 g) that separated was identified by infrared analysis.

Utility

The process may be used to generate catalytically active species such as $[o\text{-}CH_3C_6H_4O)_3P]_3NiNCCH_3$ (Gosser and Tolman, U.S. Pat. No. 3,766,231, and King, Seidel and Tolman, U.S. Pat. No. 3,798,256, and $[(C_6H_5)_3P]_3Ru(N_2)H_2$ (W. H. Knoth, U.S. Pat. No. 3,538,133). In addition, the product solutions may be used as scavengers to remove carbon monoxide or acetylene from gas streams. For example, CO, often an unwanted trace impurity in $H_2$, can be eliminated by exposure to a solution of $[(o\text{-}CH_3C_6H_4O)_3P]_3Ni$. Similarly, acetylene can be scavenged from ethylene streams.

The embodiments of the invention in which an exclusive property or privilege is claimed are defined as follows:

1. A method of making ligand deficient Group VIII metal complex compounds which comprises:
   contacting a solution containing a dissociable complex of a Group VIII metal having at least one reversibly dissociable neutral ligand of the formula:

wherein
   M is a Group VIII metal,
   L is a neutral dissociable ligand,
   the Y's, alike or different, are anionic ligands or noncoordinated counter-ions, $x$ is 3 to 6 inclusive, and $z$ is 0 to 3 inclusive with an asymmetric semipermeable membrane consisting essentially of an aromatic polymer having recurring

groups in the polymer chain, said membrane being permeable to said dissociated ligand, and applying to the solution pressure greater than the osmotic pressure of said solution whereby dissociated ligand is separated from said solution.

2. Method of claim 1 wherein L is $PR_3$, $AsR_3$, $SbR_3$, $P(OR)_3$, $RP(OR)_2$, $R_2P(OR)$ or $R_2P(NR_2^1)$, in which R and $R^1$, alike or different, are hydrocarbyl radicals of up to 12 carbon atoms having up to three substituents selected from the group aryloxy, lower alkoxy, lower alkoxycarbonyl, lower acyloxy, lower alkanesulfonyl, lower acyl, fluorine, chlorine and cyano.

3. Method of claim 2 wherein the ligand is $PR_3$.

4. Method of claim 2 wherein the ligand is

5. Method of claim 1 wherein said dissociable complex has the formula $[(o\text{-tolyl-O-})_3P]_4Ni.$ 6. Method of claim 1 wherein said dissociable complex has the formula $[(C_6H_5)_3P]_4RuH_2.$ 7. Method of claim 1 wherein said dissociable complex has the formula $[(C_6H_5)_3P]_4RuCl_2,$ and the solution is pressured with nitrogen gas.

8. Method of claim 1 wherein said dissociable complex has the formula $[(C_6H_5)_3P]_3Ru(H)[N_3(C_6H_5)_2]$ and the solution is pressured with nitrogen gas.

9. The method of claim 1 wherein the membrane is an aromatic polymer having recurring arylene groups connected by imide, amide, hydrazide or acyl hydrazide linkages in the polymer chain.

10. The method of claim 9 in which the membrane is prepared from pyromellitic dianhydride and p,p'-diaminodiphenyl ether.

11. The method of claim 9 in which the membrane is prepared from m-phenylenediamine and isophthaloyl chloride.

* * * * *

UNITED STATES PATENT OFFICE
CERTIFICATE OF CORRECTION

PATENT NO. : 3,966,595
DATED : June 29, 1976
INVENTOR(S) : Lawrence W. Gosser

It is certified that error appears in the above-identified patent and that said Letters Patent are hereby corrected as shown below:

Column 9, line 2, "$cm_+^1$" should read --$cm^{-1}$--.

Column 9, line 28, before the first line in the table insert a line which reads --<u>Anal</u>. Calcd for $C_{66}H_{56}N_3P_3Ru$;--.

Column 9, line 39, in the formula "$[n_{(C_6}h_5)_2]$" should read --$[N_3(C_6H_5)_2]$--.

Column 9, line 40, in the formula "$[N_3C_6H_5)_2]$" should read --$[N_3(C_6H_5)_2]$--.

Column 10, line 3, "$cm_+^1$" should read --$cm^{-1}$--.

Column 11, claim 4, "is" should read --is $P(OR)_3$.--.

Signed and Sealed this

Twenty-eighth Day of September 1976

[SEAL]

Attest:

RUTH C. MASON
*Attesting Officer*

C. MARSHALL DANN
*Commissioner of Patents and Trademarks*